ical Abstracts 115:116467 (1991).
United States Patent [19]

Chen et al.

[11] Patent Number: 5,419,917
[45] Date of Patent: May 30, 1995

[54] CONTROLLED RELEASE HYDROGEL FORMULATION

[75] Inventors: Chih-Ming Chen; Charles S. L. Chiao, both of Cooper City, Fla.

[73] Assignee: Andrx Pharmaceuticals, Inc., Fort Lauderdale, Fla.

[21] Appl. No.: 195,377

[22] Filed: Feb. 14, 1994

[51] Int. Cl.$^6$ .......................... A61K 9/22; A61K 9/26
[52] U.S. Cl. ................... 429/469; 424/464; 424/468; 424/488; 424/485
[58] Field of Search ............... 424/469, 488, 464, 468, 424/485

[56] References Cited

U.S. PATENT DOCUMENTS

| | | | |
|---|---|---|---|
| 4,220,152 | 9/1980 | Dresback | 128/260 |
| 4,220,153 | 9/1980 | Dresback | 128/260 |
| 4,264,573 | 4/1981 | Powell et al. | 424/19 |
| 4,361,545 | 11/1982 | Powell et al. | 424/19 |
| 4,601,894 | 7/1986 | Hanna et al. | |
| 4,657,757 | 4/1987 | Hanna et al. | |
| 4,666,705 | 5/1987 | DeCrosta et al. | 424/282 |
| 4,695,591 | 9/1987 | Hanna et al. | |
| 4,783,337 | 11/1988 | Wong et al. | 424/468 |
| 4,894,233 | 1/1990 | Sharna et al. | |
| 4,996,061 | 2/1991 | Webb et al. | |
| 4,999,226 | 3/1991 | Schock et al. | |
| 5,073,380 | 12/1991 | Babu et al. | |
| 5,082,668 | 1/1992 | Wong et al. | 424/273 |
| 5,085,865 | 2/1992 | Nayak | |
| 5,120,548 | 6/1992 | McClelland et al. | 424/273 |
| 5,133,974 | 7/1992 | Paradussus et al. | |
| 5,190,765 | 2/1993 | Jao et al. | 424/273 |
| 5,252,338 | 10/1993 | Jao et al. | 424/273 |

OTHER PUBLICATIONS

Chemical Abstracts 115:116467 (1991).
Chemical Abstracts 112:125049 (1989).
Chemical Abstracts 115:287105 (1990).
Chemical Abstracts 117:229686 (1992).
Chemical Abstracts 114:88668 (1990).
Metolose SR Brochure; pp. 1–12 (1987).

*Primary Examiner*—Shep K. Rose
*Attorney, Agent, or Firm*—Hedman, Gibson & Costigan

[57] ABSTRACT

The invention is directed to a method for the modification of the rate of release of a drug from a hydrogel which is based on the use of an effective amount of a pharmaceutically acceptable ionizable compound that is capable of providing a substantially zero-order release rate of drug from the hydrogel.

9 Claims, 2 Drawing Sheets

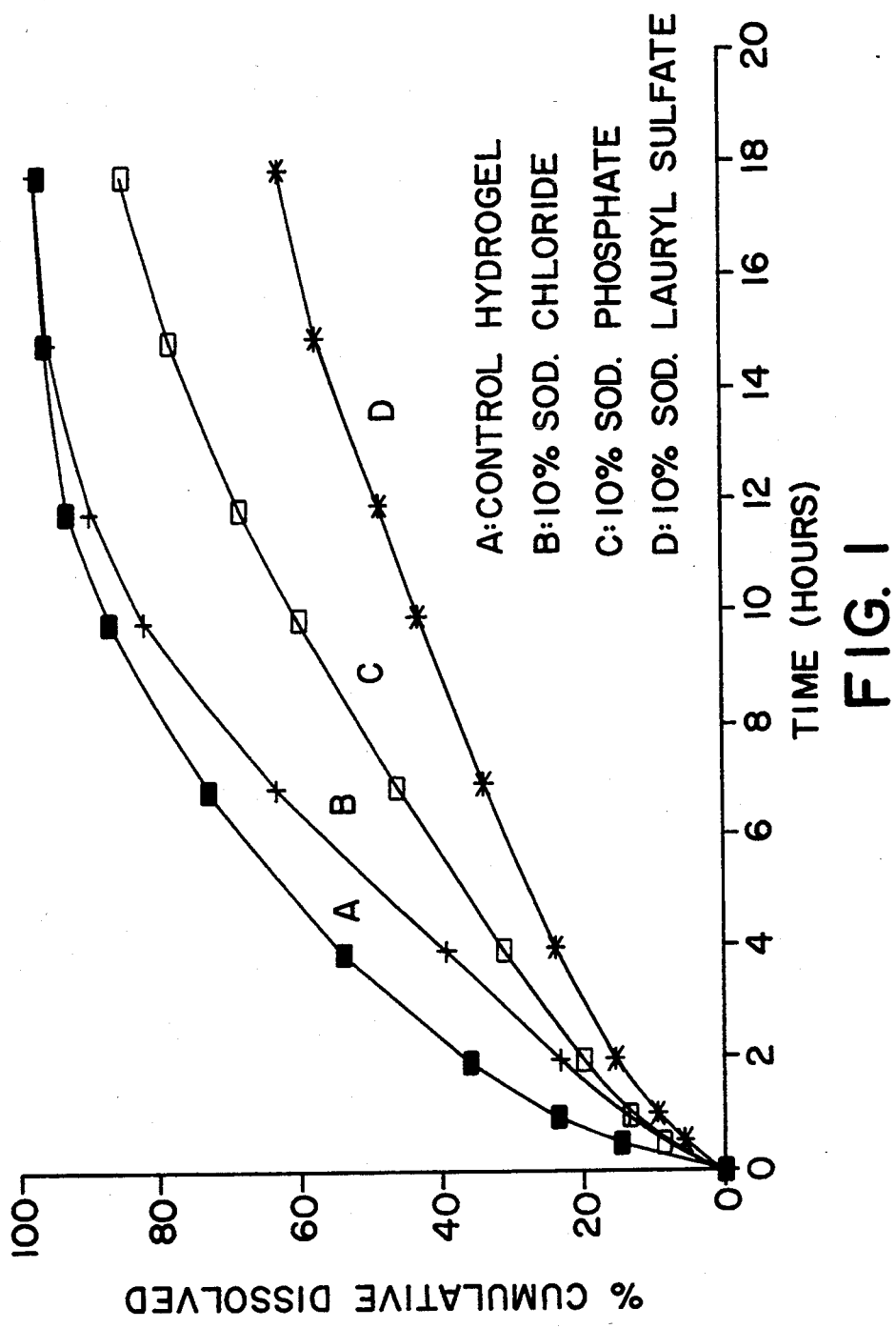

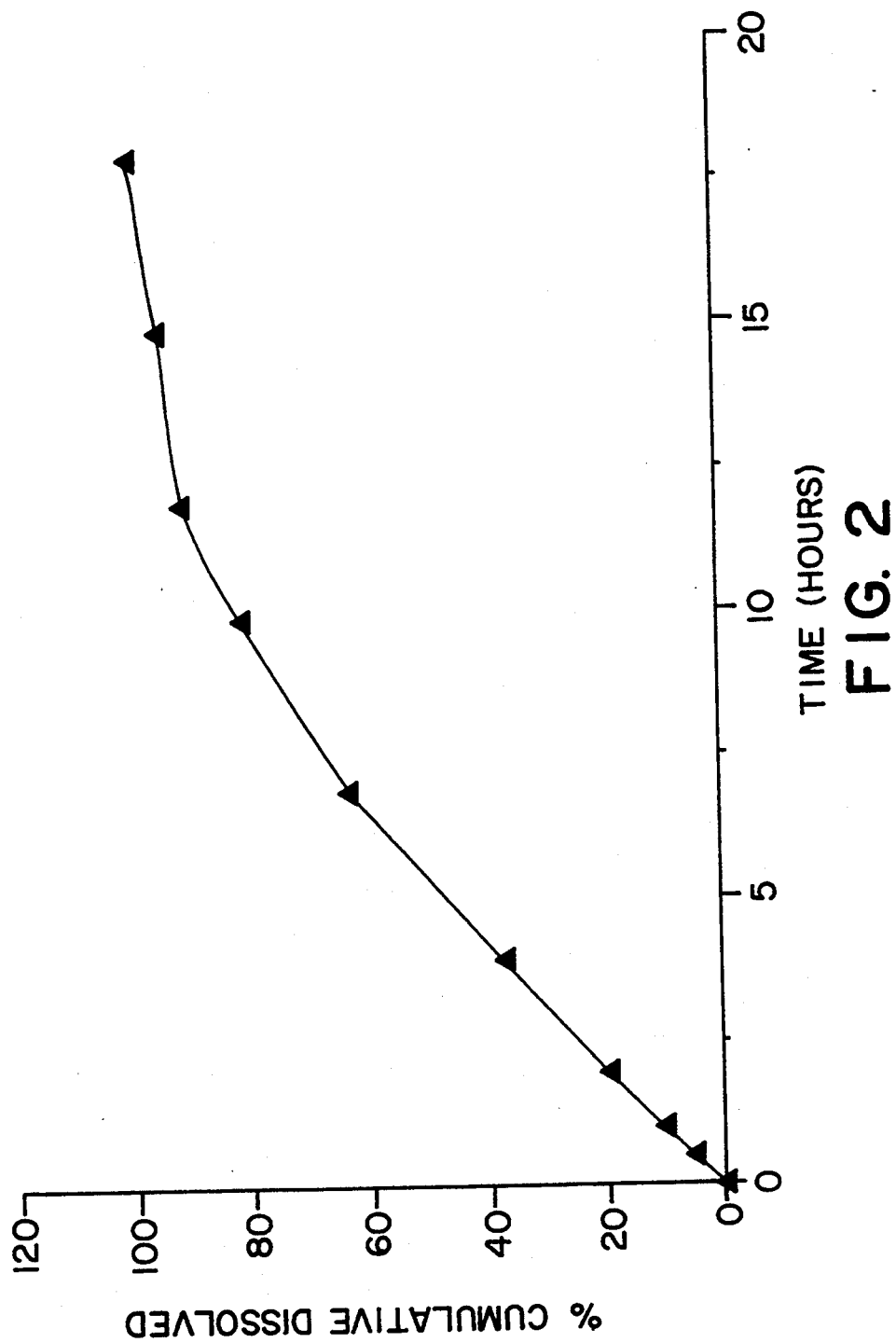

CONTROLLED RELEASE HYDROGEL FORMULATION

BACKGROUND OF THE INVENTION

The present invention is concerned with a hydrogel based pharmaceutical dosage system that provides sustained release of pharmaceuticals without the need to use special coatings or structures that add to the cost of making a sustained release formulation.

When an unmodified hydrogel is used as a pharmaceutical carrier for many diverse types of pharmaceuticals, the in vitro release rates are not zero-order release rates because the initial rate of release of the drug tends to be much higher than the subsequent rate of release of the drug.

In the prior art, hydrogels have been used to prepare sustained release formulations. These formulations have commonly exhibited an "initial burst effect" which causes a non-linear release rate of a drug. In order to avoid the initial burst effect, hydrogels have been used in combination with mechanical devices and polymeric coatings to control the rate of drug release in order to modify the release rate characteristics and provide a substantially zero-order controlled release formulation.

The present invention provides a method for modifying the release characteristics of a hydrogel by adding an effective amount of an ionizable compound to the hydrogel and drug formulation.

SUMMARY OF THE INVENTION

The invention comprises a method for the modification of the rate of release of a drug from a hydrogel which is based on the use of an effective amount of a pharmaceutically acceptable ionizable compound that is capable of providing a substantially zero-order release rate of drug from the hydrogel.

Accordingly it is a primary object of this invention to provide a method for the modification of the rate of release of a drug from a hydrogel.

It is also an object of this invention to provide a modifier for the rate of release of a drug from a hydrogel which will modify the rate of release of a drug from the hydrogel.

It is also an object of this invention to provide a novel controlled release pharmaceutical dosage unit which does not require the use of a wax or a water insoluble resin coating.

These and other objects of the invention will become apparent from a review of the appended specification.

BRIEF DESCRIPTION OF THE DRAWINGS

FIG. 1 is a graphical representation of the release rates of tablets of diltiazem hydrochloride which are based on unmodified hydrogel, i.e., hydroxypropylmethyl cellulose and a modified hydrogel which that has been modified by the addition of certain ionizable compounds that are capable of modifying the rate of release of a drug from a hydrogel.

FIG. 2 is a graphical representation of the release rate of a tablet prepared as described in Example 2.

DETAILED DESCRIPTION OF THE INVENTION

The hydrogel that is the basis of the formulation of the present invention is any hydrogel which causes a drug to exhibit a substantially zero-order release rate when the hydrogel is modified by the addition of an effective amount of a non-toxic, pharmaceutically acceptable ionizable compound which is capable of modifying the release rate of the drug from the hydrogel.

Suitable hydrogels include hydroxypropylmethyl cellulose, sodium alginate, xanthan gum and the like.

The ionizable compound may be any non-toxic inorganic or organic compound that is compatible with the hydrogel and affects the dissolution rate of a tabletted drug that includes a drug, a hydrogel and said ionizable compound. The ionizable compound should have a pH in water of from about 2 to not greater than about 11 and preferably a pH of from 4–8 when one molar equivalent is dissolved in 1 liter of water. The ionizable compounds include alkali metal chlorides, magnesium chloride, calcium chloride, organic acids such as citric, succinic, fumaric, malic, maleic, glutaric, lactic and the like, alkali metal sulfates such as sodium sulfate, alkali metal alkyl sulfates wherein the alkyl group is from 1 to 14 carbon atoms, such as sodium methyl sulfate, sodium lauryl sulfate and the like as well as dioctyl sodium sulfosuccinate, dihydrogen sodium phosphate and monohydrogen sodium phosphate. It is to be understood that the ionizable compound may be a single compound or a mixture of two or more materials that provide the desired release characteristics.

Any drug may be used in the practice of the invention which is compatible with the hydrogel and exhibits a substantially zero-order controlled release when tabletted with the hydrogel and an effective amount of the non-toxic, pharmaceutically acceptable ionizable compound. Examples of drugs that may be utilized are the calcium channel blocking drugs such as diltiazem hydrochloride and verapamil hydrochloride. The dosages to be employed are sufficient to maintain a therapeutic level of the drug in a patient. Generally the amount of the ionizable compound that is employed will be between 1 and 50% and preferably 5 to 15% by total weight of the hydrogel forming material, the drug and the ionizable compound. The drug will generally be from 10 to 90% by total weight of the hydrogel forming material, the drug and the ionizable compound. The hydrogel will be the difference of the total weight of the formulation less the combined weight of the drug and the ionizable compound. When hydroxypropylmethyl cellulose and sodium chloride are employed to prepare a tablet formulation of diltiazem, it has been found that a blend of 26.09 g of diltiazem hydrochloride; 6.5 g of sodium chloride; 3 g of sodium lauryl sulfate and 30 g of hydroxypropylmethyl cellulose may be employed to provide a substantially zero-order release tablet.

The amount of the hydrogel and the ionizable compound that are used may be determined by preparing a series of tablets using varying amounts of hydrogel and ionizable compound in combination with the selected drug. The release characteristics may be determined separately using simulated gastric fluid (pH 1.2-without enzymes); simulated intestinal fluid (ph 7.5-without enzymes) and a pH 6.2 buffer solution. The "paddle method" from USP XXII which is incorporated by reference, may be used to determine the release characteristics of a given formulation and by the addition of or subtraction of incremental amounts of the ionizable compound to a particular tablet formulation, the release curve for a particular drug may be shifted to a zero-order release product.

The pharmaceutical compositions of the invention will contain an effective amount of the drug and an amount of the hydrogel and ionizable compound that may be made into tablets which will have a substantially zero-order release of the selected drug. In addition to the hydrogel and ionizable compound, the tabletted product may contain an inert solid diluent such as lactose, dextrose, maltose, fructose, corn starch, rice starch and the like. Other conventional additives such as binding agents such as polyvinylpyrrolidoine, starch, gelatin, microcrystalline cellulose and the like may be added to the tablet formulation. In addition, it is contemplated that coloring agents, stabilizers, lubricants such as stearic acid, palmitic acid, magnesium stearate, and the like may be added to the tabletting composition in amounts which are determined to produce the desired effect.

Tablets may be made using conventional tabletting machines and appropriately sized dies.

DESCRIPTION OF THE PREFERRED EMBODIMENT

The following examples are intended to illustrate the invention without limiting the scope of the invention:

EXAMPLE 1

A blend of diltiazem hydrochloride dispersed in hydroxypropylmethyl cellulose (HPMC) (100,000 cps as measured in a 2 wt % solution in water) was prepared by first separately passing the ingredients through a #40 US Standard mesh sieve and thereafter blending the mixture in a V-blender for 5 minutes. The blend was identified as Blend A and this blend had the following formulation:

| Ingredient | |
|---|---|
| Diltiazem HCl | 36.9 wt % |
| HPMC (Methocel K100M) | 27.0 wt % |
| Lactose, Anhydrous | 35.1 wt % |
| Magnesium stearate | 1.0 wt % |

The powder was blended and compressed into capsule shaped tablets ( 0.70"×0.29") with the compression set at two tons. An in vitro dissolution test was carried out separately using 900 ml of an enzyme free simulated gastric fluid (pH 1.2); 900 ml of an enzyme free simulated intestinal fluid (pH 7.5) and a buffer solution (pH 6.2) substantially as described in USP XXII. The USPXXII method that was used was apparatus No. 2. The dissolution curve was prepared by determining at preset intervals the amount of dissolved diltiazem. The results are shown on FIG. 1 as curve A.

Using the same procedures that were described above, tablets were prepared which contained 10% by weight of sodium chloride (B); 10% by weight of $Na_2HPO_4$ (C); 10% by weight of sodium lauryl sulfate (D) in place of 10% by weight of the anhydrous lactose that was employed in Blend A. The dissolution characteristics were determined according to the procedure set forth above and the characteristics are curves B, C and D of FIG. 1, respectively. The presence of the ionizable compound has the effect of flattening the release curve by preventing the initial burst of the active drug which results when a tablet, made from unmodified HPMC, is employed with diltiazem hydrochloride.

EXAMPLE 2

Using the procedure set forth in Example 1, tablets were made from the following Formulation:

| Ingredient | |
|---|---|
| Diltiazem HCl | 26.09 wt. % |
| HPMC (Methocel (K100M) | 30.00 wt. % |
| Lactose, Anhydrous | 33.39 wt. % |
| Sodium Chloride | 6.52 wt. % |
| Sodium Lauryl Sulfate | 3.00 wt. % |
| Magnesium Stearate | 1.00 wt. % |

The ingredients were blended and compressed into 0.28" round tablets using the procedure described in Example 1. The tablets were tested according to the procedure of Example 1 and the dissolution curve is set forth in FIG. 2. The results show that the tablets produced according to Example 2 have a substantially zero-order release rate.

EXAMPLE 3

Using the procedures of Example 1, tablets having the following composition are prepared:

| Ingredients | |
|---|---|
| Verapamil HCl | 40.00 wt. % |
| HPMC | 22.22 wt. % |
| Sodium Chloride | 10.00 wt. % |
| Lactose, Anhydrous | 26.78 wt. % |
| Magnesium stearate | 1.00 wt. % |

The ingredients are blended and compresed using the procedure described in Example 1.

We claim:

1. A method of making an extended zero order controlled release tablet formulation, said method consisting essentially of:
   (a) combining a drug and a hydrogel forming agent selected from the group consisting of hydroxypropylmethyl cellulose, sodium alginate and xanthan to form a mixture, said hydrogel containing an effective amount of a non-toxic, pharmaceutically acceptable ionizable compound which is sufficient to impart zero-order release characteristics to said hydrogel said ionizable compound being selected from the group consisting of alkali metal chlorides, organic acids, alkali metal sulfates and alkali metal alkyl sulfates, dihydrogen sodium phosphate and monohydrogen sodium phosphate said composition being free from wax or water insoluble resins; and
   (b) thereafter tabletting said mixture to form tablets having substantially zero-order controlled release characteristics.

2. A method as defined in claim 1 wherein the hydrogel is hydroxypropylmethyl cellulose.

3. A method as defined in claim 2 wherein the ionizable compound is a mixture of sodium chloride and sodium lauryl sulfate.

4. A method as defined in claim 3 wherein the drug is diltiazem hydrochloride.

5. An extended zero order release pharmaceutical composition in the form of a compressed tabletted blended mixture which consists essentially of:
   (a) a drug;
   (b) a hydrogel forming agent selected from the group consisting of hydroxypropylmethyl cellulose, sodium alginate and xanthan; and
   (c) an effective amount of a non-toxic, pharmaceutically acceptable ionizable compound which is compatible with said drug and said hydrogel said ionizable compound being selected from the group consisting of alkali metal chlorides, organic acids, alkali metal sulfates and alkali metal alkyl sulfates, dihydrogen sodium phosphate and monohydrogen sodium phosphate said composition being free from wax or water insoluble resins.

6. A pharmaceutical composition as defined in claim 5 wherein the drug is selected from the group consisting of diltiazem and verapamil.

7. A pharmaceutical composition as defined in claim 6 wherein the hydrogel forming agent is hydroxypropylmethyl cellulose.

8. A pharmaceutical composition as defined in claim 7 wherein the non-toxic, pharmaceutically acceptable ionizable compound which is compatible with said drug and said hydrogel is sodium chloride.

9. A pharmaceutical composition as defined in claim 7 wherein the non-toxic, pharmaceutically acceptable ionizable compound which is compatible with said drug and said hydrogel is disodium hydrogen phosphate.

* * * * *